United States Patent

Randhahn et al.

[11] Patent Number: 5,594,161
[45] Date of Patent: Jan. 14, 1997

[54] METHOD AND APPARATUS FOR RAPIDLY TESTING THE INTEGRITY OF FILTER ELEMENTS

[75] Inventors: Horst Randhahn, Darmstadt-Eberstadt; Hartmut Vogelman, Dreieich, both of Germany

[73] Assignee: Pall Corporation, East Hills, N.Y.

[21] Appl. No.: 395,289

[22] Filed: Feb. 27, 1995

Related U.S. Application Data

[63] Continuation of Ser. No. 142,431, filed as PCT/EP93/00718, Mar. 24, 1993, published as WO93/19356, Sep. 30, 1993, abandoned.

[30] Foreign Application Priority Data

Mar. 24, 1992 [DE] Germany ............................ 42 09 519.0

[51] Int. Cl.$^6$ .................................................. G01N 15/08
[52] U.S. Cl. ................................................................ 73/38
[58] Field of Search ........................... 73/38, 40; 210/741, 210/85, 90, 92, 323.1, 323.2

[56] References Cited

U.S. PATENT DOCUMENTS

| | | | |
|---|---|---|---|
| 4,384,474 | 5/1983 | Kowalski | 73/38 |
| 4,449,392 | 5/1984 | Huschke | 73/38 |
| 4,511,471 | 4/1985 | Müller | 210/323.2 |
| 4,614,109 | 9/1986 | Hofmann | 73/38 |
| 4,701,861 | 10/1987 | Kauke | 73/38 |
| 4,872,974 | 10/1989 | Hirayama et al. | 73/38 |
| 4,881,176 | 11/1989 | Kononov | 364/500 |
| 4,909,937 | 3/1990 | Hoffmann et al. | 210/315 |
| 5,005,430 | 4/1991 | Kibler et al. | 73/863.01 |
| 5,064,529 | 11/1991 | Hirayama et al. | 210/90 |
| 5,353,630 | 10/1994 | Soda et al. | 73/38 |

FOREIGN PATENT DOCUMENTS

| | | |
|---|---|---|
| 392158 | 2/1991 | Austria . |
| 0139202 | 5/1985 | European Pat. Off. . |
| 0314822 | 2/1987 | European Pat. Off. . |
| 3342440 | 11/1983 | Germany . |
| 3805361 | 2/1988 | Germany . |
| 3917856 | 6/1989 | Germany . |
| 57-102212 | 9/1982 | Japan . |
| 2127559 | 4/1984 | United Kingdom . |
| 2132366 | 7/1984 | United Kingdom . |
| WO90/04445 | 10/1989 | WIPO . |

Primary Examiner—Michael Brock
Attorney, Agent, or Firm—Leydig, Voit & Mayer

[57] ABSTRACT

A method of testing the integrity of a filter element in a falter assembly includes a) wetting filter material of a filter element having an inlet side and an outlet side connected to an outlet conduit, b) subjecting the inlet side of the filter element to a gas pressure, c) measuring the pressure in the outlet conduit as a function of time, with a downstream outlet valve for the outlet conduit being closed, and d) determining whether the pressure measured at a preselected time exceeds a reference pressure by a predetermined amount, or determining whether the time required to reach a preselected pressure is shorter than a reference time by a predetermined amount.

30 Claims, 3 Drawing Sheets

METHOD AND APPARATUS FOR RAPIDLY TESTING THE INTEGRITY OF FILTER ELEMENTS

This application is a continuation of application Ser. No. 08/142,431, filed as PCT/EP93/00718 Mar. 24, 1993 and published as WO93/19356 Sep. 30, 1993, now abandoned.

BACKGROUND OF THE INVENTION

1. Field of the Invention

The present invention relates to a method and apparatus for testing the integrity of filter elements in a filter assembly. The invention is particularly applicable to filter systems comprising a very large number of filter elements where the determination of a defective element among so many elements becomes difficult.

2. Description of the Related Art

Large dimensioned filter systems of various construction are known in which 100 or more filter elements are arranged in one large filter housing. In many applications, for example, in the food and beverage industry or in the pharmaceutical industry, large scale filtration also has to be carried out under sterile conditions. Not only the filter housing but the filter elements along with the filter material must be regularly sterilized. Such sterilization performed for example with hot water or steam can deteriorate the integrity of the filter material, especially when as the sterilization has to be carried out frequently.

Deterioration of the filter material and/or other parts of the filter element can also arise in other applications, for example, when chemically aggressive substances or high temperature gases are to be filtered. The deterioration of the filter element can occur in the form of the filter material itself being degraded or a joining of the filter material to the filter housing may become defective and act as a by-pass, i.e. furnish an opening greater than the pore size of the filter material.

In actual practice, the filter elements are often built into filtration systems which are an integral part of some production operations. It would be a considerable drawback if the operation had to be shut down and the filtration system had to be dismantled to inspect the filter integrity at given service intervals. A fast and convenient method is needed of in situ testing in built-in systems, which requires little down time of the filtration operation.

In large filter systems, just one or more defective filter elements can lead to a substantial bacteria contamination of the filtered fluid and possibly the shut-down of the filtration operation. Finding the particular element or elements responsible among the 100 or more elements can be a very time-consuming task, particularly if this is done on a trial and error basis. Means of locating the defective elements in a systematic way are needed.

SUMMARY OF THE INVENTION

An object of the present invention is therefore to provide a rapid and simple method of testing one or more filter elements in a filtration system without need of disassembling the system.

Another object of the invention is to provide a method of testing the integrity of a large number of filter elements and a filter assembly for carrying out the method by which damaged filter elements can be isolated in a rapid, systematic and efficient manner.

A method of testing the integrity of at least one filter element in a filter assembly is provided as defined in the claims. The filter element or elements are connected to a common outlet conduit. After wetting the filter material of the at least one filter element, a gas pressure is applied to the inlet side and preferably the diffusive flow through the wetted filter material measured. The pressure is then measured in the outlet conduit as a function of time, where valve means further downstream in the outlet conduit are closed. According to the method, it is then determined whether the pressure measured at a preselected time exceeds a reference pressure by a pre-determined amount.

In an alternative embodiment, the time required to reach a preselected pressure is measured and compared with a reference time to determine whether the filter is intact or not, again when the outlet valve is closed.

In a further embodiment, the at least one filter element comprises a plurality of filter elements which are subdivided into a plurality of filter sections or clusters. The filter elements belonging to each section are connected to a common outlet conduit.

The method comprises the steps of wetting the filter material (preferably with water). The filter elements of all sections having wetted filter material are then subjected to a gas pressure, preferably air pressure, as the test pressure. The pressure in the outlet conduit for each of the plurality of filter sections is then measured as a function of time, with closed outlet valves. Preferably, the diffusive flow rate across the wetted filters is also measured. The measured outlet pressure at a certain time is then compared with a reference pressure for each of the sections. If the measured pressure exceeds the reference value, this is an indication that the filter material or filter element itself in some way is not completely intact.

In an alternative embodiment of the same method, the pressure again is measured in the outlet conduit means for each filter element section. In this case however the time is measured to reach a preselected pressure. If this time is shorter than a maximum time for that pressure, this again indicates that the resistance of the filter material is not sufficient, i.e. is in some way defective.

The method preferably further includes measuring the gas flow rate through the wetted filter material under the test gas pressure. Measuring the flow rate as well as the pressure build-up as a function of time allows a more sensitive test. Temperature fluctuations for example during the test which would lead to a falsification of the results can be detected and accounted for. The method can also be carded out in systems which operate continuously under pressure, for example, above atmospheric pressure. The pressure build-up as a function of time is then observed in the outlet conduit added on to the pressure already existing in the system. In this embodiment, one only need adjust the gas pressure to give a sufficient pressure gradient across the wetted filter material to allow for a reliable test.

In the embodiment with a plurality of filter elements arranged in subsections, the pressure time behavior in each section can be measured simultaneously with the proper instrumentation.

In this manner, a large number of filter sections each comprising several filter elements can be measured in very short time. Each section or cluster will typically comprise 2 to 15 filter elements, particularly 3 to 7 filter elements. The test procedure then has the advantage that individual sections can be checked simultaneously and rapidly. Once the defective section is isolated, the individual elements of this section being smaller in number can also be tested rapidly.

In accordance with the present invention, a filter assembly is also provided for carrying out the above method as defined in the claims. The filter assembly comprises a plurality of filter elements sub-divided into a plurality of sections, each section containing a portion of the filter elements (preferably 3 to 7 filter elements). Each section has an outlet header and an outlet conduit connected thereto. The outlet sides of the filter elements are connected to the header of each section. Pressure sensing means are arranged to measure the pressure in the outlet conduit of each of the sections.

In a further embodiment, valve means are arranged downstream of the pressure sensing means in each of the outlet conduits. In this manner, gas passage can be opened or closed individually for each of the plurality of filter sections. The location of the valve means downstream of the pressure sensing devices allows measuring of the pressure build-up in each section as a function of time as defined in the above integrity test method.

In a further embodiment, the plurality of filter elements are arranged in a common vessel containing the fluid to be filtered, where each filter element has a filter material surface which is in direct contact with the influent fluid. This arrangement of the filters provides that the gas pressure applied during the integrity test to the filter inlet surface is the same for all filter elements.

BRIEF DESCRIPTION OF THE DRAWINGS

Further objects and advantages of the present invention will become apparent through the following description of preferred embodiments in conjunction with the drawing.

DESCRIPTION OF PREFERRED EMBODIMENTS

Figure 1:
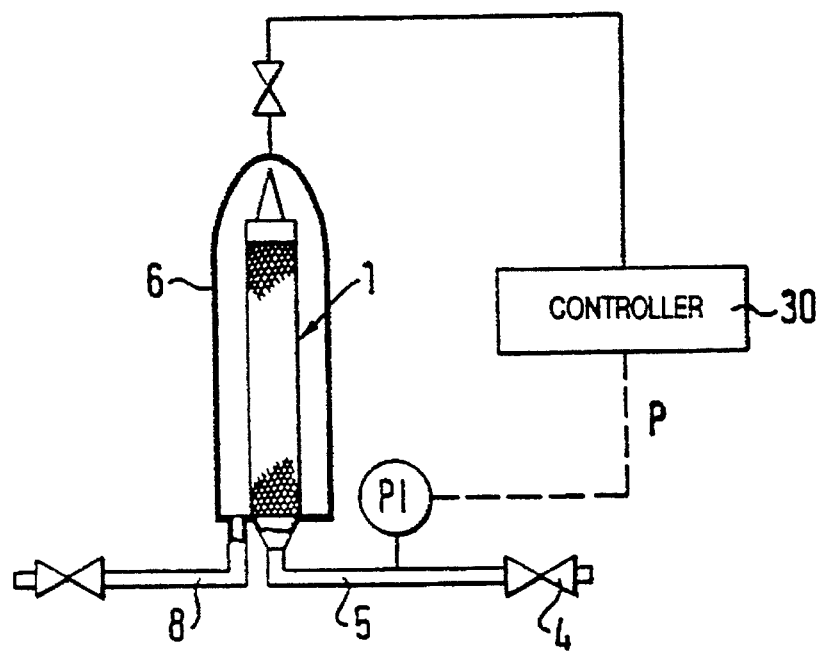
FIG. 1 shows a simple filtration system for explanation of the basic method of the present invention.
Figure 2:
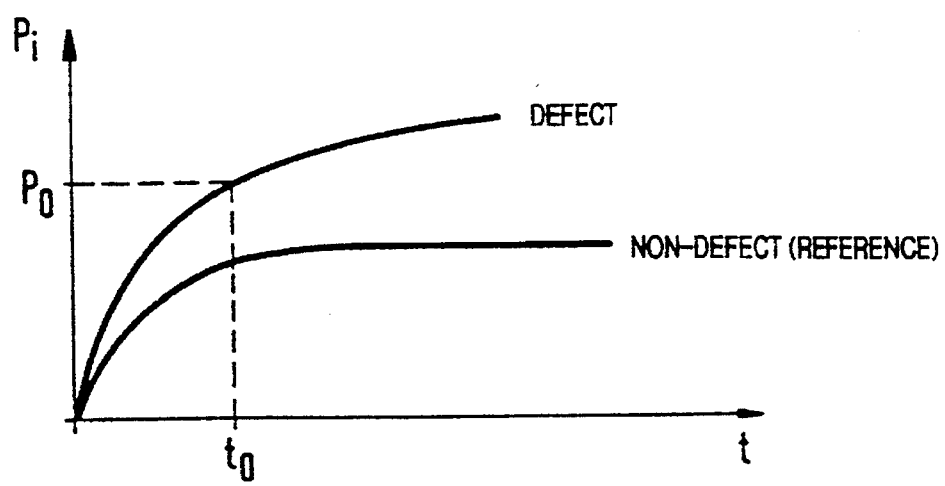
FIG. 2 shows an example of the pressure build-up as a function of time in the integrity test.

The method of the present invention is first explained in conjunction with FIGS. 1 and 2 where only a single filter element 1 is involved. The inlet conduit 8 provides a fluid to be filtered to the inner volume of the vessel 6. After passing the filter element 1, the filtrate leaves the vessel 6 through the conduit 5. A pressure sensor PI is located in the conduit 5 which is connected electrically to a measurement and control system 30.

The integrity test will normally begin after a cleaning or sterilization procedure of the filtration system. The filter material of the filter element 1 is wetted with an agent, preferably water, as a first step of the procedure. A test gas pressure is then established on the inlet side of the filter element, i.e. in the interior of the vessel 6. It is preferred that the test pressure be held constant, which can be accomplished with the control means 30. The preferred gas is air. The preferred test pressures are in the range of 50 to 6000 mbar, more preferably 500 to 5200 mbar.

The applied gas pressure results in diffusion of the gas through the wetted filter material and consequently a pressure build-up on the outlet side or clean side of the filter element. The outlet valve 4 is closed during the test. This pressure build-up as a function of time is measured with the pressure sensor PI located in the conduit 5.

The pressure signal is recorded and analyzed in the control unit 30. A typical pressure-time behavior is shown in FIG. 2. Pressure build-ups are shown for an intact filter element and one which has a defect. With a defect, a damaged portion of the filter material allows direct fluid passage and therefore the faster pressure build-up as a function of time.

According to one embodiment of the invention, the control unit 30 compares the measured pressure at a time $t_0$ with a reference pressure, for example as indicated in FIG. 2. If the measured pressure $P_0$ exceeds the reference pressure by a pre-determined mount, this is an indication that something in the filter is indeed defective. The reference curve of FIG. 2 will depend on the filter material as well as the dimensions of the filter system including the conduit 5. The reference curve will normally be determined empirically, for example when the filter system is first put into operation.

In another embodiment, the control unit 30 determines the time required to reach a preselected pressure and then compares this with a reference time. If the measured time is shorter than the reference time by a predetermined mount, this again is an indication of a defective filter element.

In addition, the flow rate Q of gas diffusion through the wetted material can be measured simultaneously with the pressure build-up measurement. Apparatus and methods for supplying the test pressure and measuring the diffusion flow rate are known for example from EP-A 314 822, which are preferably employed here. The pressure-time behavior of the test gas is monitored which serves as a parameter for automatic supply of differential volumes of fluid to the test chamber. The size of the selected volumes supplied are varied until the desired supply rate is achieved. The supply rate in turn corresponds to the diffusion flow rate across the wetted filter elements.

Having knowledge of the diffusion flow rate, temperature fluctuations which could arise during the test procedure are detected. For example, if the equipment has previously been sterilized and has not sufficiently cooled off, a small change of even a few °C. can falsify the pressure measurement. The pressures measured in the outlet conduit 5 are in the order of 10 to 60 mbar, i.e. relatively small and sensitive to temperature changes. If a high pressure is found indicating a defective element, the flow rate Q at this time is also checked to see if the pressure is consistent with the momentary flow rate. If this is not the case it indicates that a temperature change has taken place and the test is then stopped and repeated after the temperatures have stabilized.

It is also possible to carry out the tests when the vessel is under a normal operating pressure. For example, a pressure higher or lower than atmospheric pressure could exist in the outlet conduit under normal operating conditions of the filtration system. In the test procedure then, the applied gas pressure would represent a pressure gradient between the interior of the vessel and the outlet conduit 5. The pressure build-up could then still be determined as a function of time in the outlet conduit 5, where in this case the base pressure is something other than atmospheric pressure. The vessel could have an over pressure or could even be in the vacuum range.

The above method can be applied to installed systems. The test itself normally lasts from 5 to 20 minutes, preferably about 10 to 15 minutes. No dismantling of the filtration system is necessary, the test is performed in situ. Connections of course are necessary to supply the wetting agent for the filter material and to supply the test gas pressure. These connections however will normally be present in the existing system.

The above described method has particular advantages in filtration systems comprising a plurality of filter elements. Such an embodiment will now be discussed in conjunction with FIG. 3. A plurality of filter elements 1 are arranged in a homing shown in the form of a large vessel 6. An inlet conduit 8 communicates with the inner volume of the vessel 6. After passing the filter elements 1, the titrate leaves the vessel 6 through the conduits 5. Outlet header 7 collects the outgoing filtrate.

Figure 3:
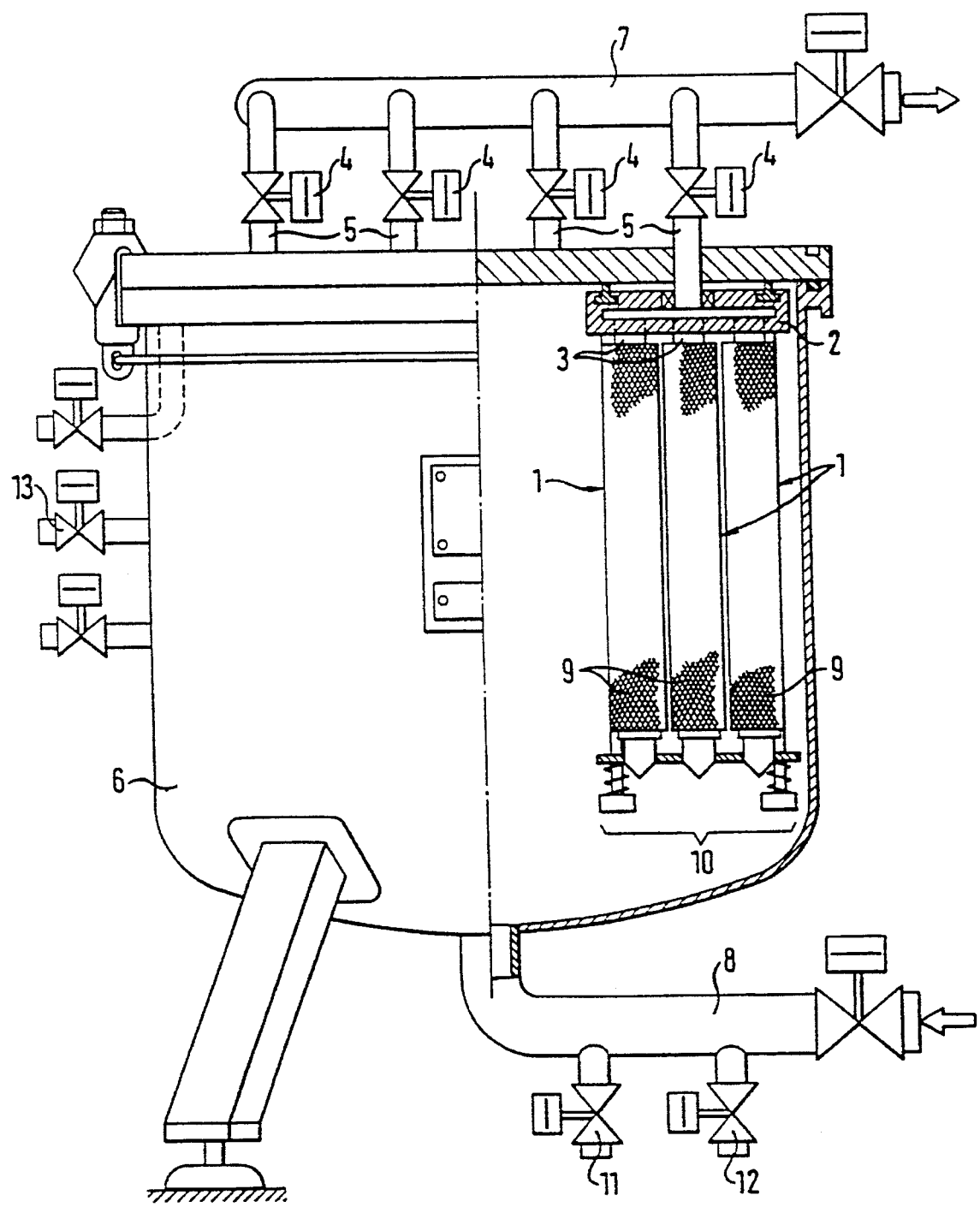
FIG. 3 shows an embodiment of the filter assembly of the present invention comprising a plurality of filter elements sub-divided into separate filter sections.
Figure 4:
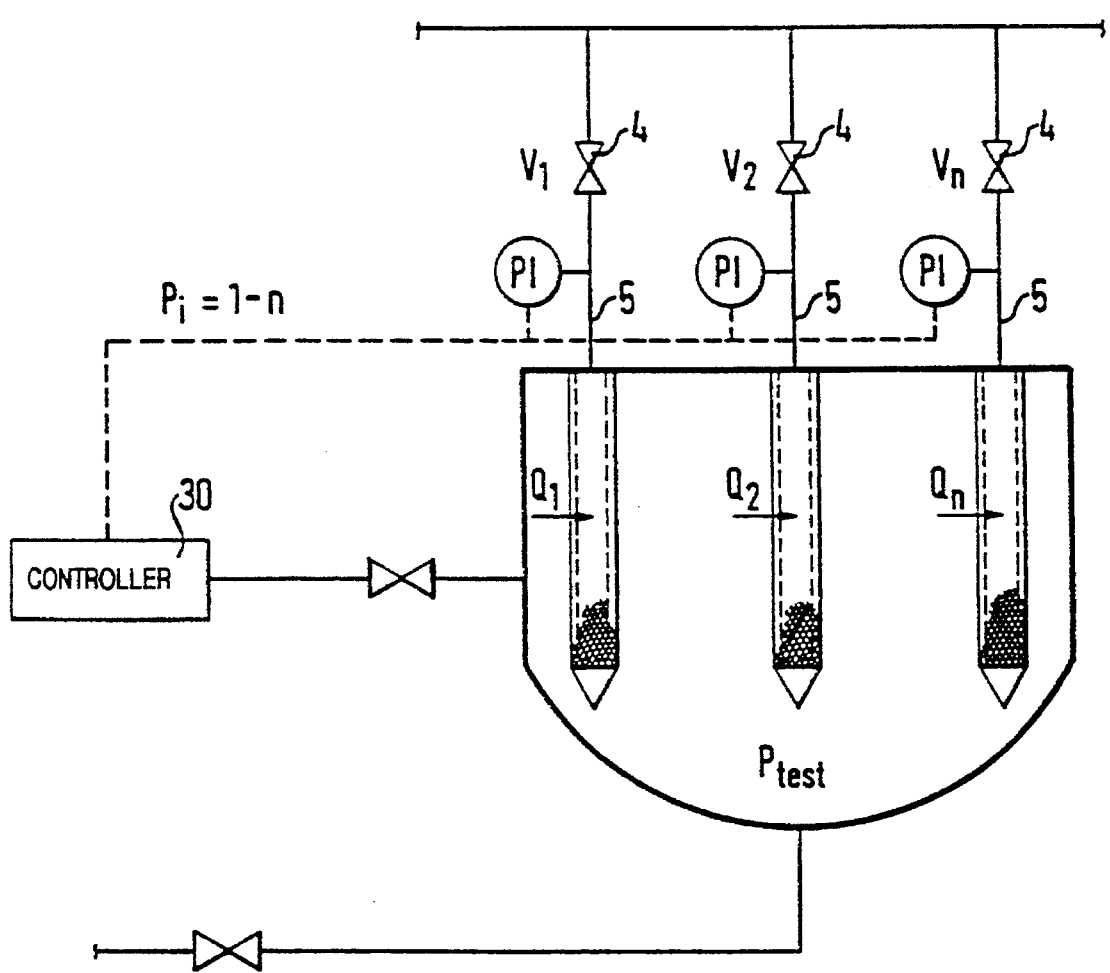
FIG. 4 shows a schematic diagram of the set-up for the integrity test method when a plurality of filter elements is involved.

The filter assembly further comprises an outlet header 2 which is connected to the individual outlet openings 3 of the filter elements 1. The filter elements are divided into a number of sections or clusters 10 each having one outlet header 2. Only one section is illustrated in FIG. 3. In the embodiment of FIG. 4, three such sections of filter elements are illustrated. The filter assembly of the invention further comprises pressure sensing means in the outlet conduits 5 as indicated in FIG. 4. The filter assembly also comprises valve means 4 located in the outlet conduits 5. The pressure sensing means are located upstream of the valves 4.

The valve means 4 can be any suitable type of valve, preferably valves which can be employed in a computer-controller automated system. Such valves include ball valves, clack valves or membrane valves. The headers or adapters 2 are designed to connect to the outlet openings 3 of a predetermined number of filter elements 1. In this arrangement, gas flow through all of the elements 1 in the section 10 can be controlled by the single valve 4 in the outlet conduit 5. Several sections 10 or all sections of the filter elements can be dosed off simultaneously. The filter elements in such filter systems are generally of cylindrical form, whereby the outer portion of the cylinder is made up of the filter material. As shown in FIG. 1, the outer surface 9 of the filter material is in direct contact with the interior of the vessel 6. The filter elements can be mounted onto the outlet header 2 in any convenient manner. The outlet header is preferably formed of a synthetic material, PVDF is particularly preferred.

The filter assembly of the present invention is suited for applications in industry-where the filter elements may be damaged through purification, decontamination or sterilization procedures which are necessary for reasons of product quality. For example in the beverage industry absolutely sterile conditions are required. After a production time, i.e. filtration operation time, of one or more days, such systems must be evacuated and subjected to a sterilization treatment. The filter elements may be damaged due to the high temperatures and pressures used in sterilization, which is normally carried out with steam and/or hot water. If the filter elements do not withstand such treatment or their material structure is altered, the specified and validated removal efficiency may no longer be available when the operation of the system is restarted.

According to a further embodiment of the above described method, the integrity of the filter elements can be tested at this point, i.e. before restart of the filter operation. The integrity of the filter elements is tested in situ in a filter assembly sub-divided into a plurality of sections as described above. The test is based on the gas diffusion through liquid wetted filter elements. One important application of this method is sterile filter operations where microorganisms should be retained by the filter material. In this case, the pore size of the filter material must remain correspondingly small, in other words the sterilization treatment should not enlarge the pore sizes to the extent that microorganisms could pass the filter material.

The test involves an initial wetting of the filter material, preferably with water for hydrophilic membranes. If the filter material is hydrophobic, the wetting agent is preferably a solvent or alcohol or a liquid mixture of low surface tension. Wetting can be performed by filling the vessel 6 with the wetting agent through an inlet connection 11, followed by draining the vessel through an outer connection 12. The wetting agent is selected depending on the filtration problem and the correspondingly selected filter material.

After wetting, the filter elements are subjected to a fluid pressure. The test fluid can be supplied through the conduit 13 of FIG. 3. Depending on the application, the fluid can be a gas or a liquid, although a gas is particularly preferred. Suitable gases include air or nitrogen. The preferred medium is air.

As described in conjunction with FIG. 1, gas is supplied to the interior of the vessel at a pressure in the range of 50 to 6000 mbar. The test pressure is preferably held constant during the testing. The valves 4 are set to their dosed position. The pressure measuring means (PI) are arranged to measure pressure build-up on the downstream or clean side of the filter elements. The pressure sensors PI are connected to measurement and control means 30 shown in FIG. 4. The measurement and control means 30 are also arranged to maintain the test pressure constant throughout the procedure.

The desired test pressure to be set will depend on the filter material or type of filter elements being tested. It will also depend on the possible condition of the filters, whether they have been in operation over a longer period or on other operational parameters.

The control means 30 measure the time dependence of the pressure build-up as shown in FIG. 2, but now for each filter sub-section. At a preselected time $t_o$, the control unit 30 compares the pressure actually measured at that time ($P_o$) with a reference pressure, as discussed above in conjunction with FIG. 2. If the measured pressure $P_o$ exceeds the reference pressure, this means that the pressure resistance of the filter medium is not sufficient, in other words there is some defect in one of the elements of this filter section. In practice, the control unit 30 determines whether the measured pressure $P_o$ greater than a reference pressure by a pre-determined mount. If this is the case, at least one of the filters in that sub-section of the filter element will have to be isolated and replaced.

In an alternative embodiment, the control unit 30 can determine the time required to reach a preselected pressure. If this time is shorter than a reference time for that pressure, then this also is an indication that at least one of the filter elements in this sub-section is defective.

The reference curve shown in FIG. 2 will also depend on the operational set-up, i.e. the dimensions of the filter assembly, the number of filter elements and in particular the number of filter elements per sub-section or cluster. The reference pressure for comparing with the measured pressure can be a pre-set fixed value which is entered into the control unit 30 for the comparison. The fixed value can be determined empirically or through calculations when the filtration system is put into operation.

Alternatively the reference pressure can be the pressure measured in one of the other of the plurality of filter sections. Preferably, the reference pressure is an average of the pressure measured in at least two of the other filter sections. Such filter systems will normally have 10 to 16 clusters. By respectively comparing the pressure build-up behavior of one section with the other sections, it can readily be discerned whether one section or cluster deviates considerable from the others. This procedure assumes that the number of filter elements per section is the same and the flow and pressure conditions are otherwise very similar which will normally be the case. The approach is most favorable since no predetermined empirical determinations need be made.

The measurement of the pressure build-ups $P_i$ for each sub-section $i=1,2,\ldots,n$ according to FIG. 4 can also be done simultaneously with a measurement of the diffusion flow rate through all of the filters, i.e. the sum $Q1+Q2+\ldots+Qn$. Such flow rate measurements are necessary for validation of filtration systems. However, since only the total flow rate through all elements in all sections is normally measured, it can still be possible that individual filter elements are defective and would not meet the validation requirements. The present method then offers an extension of previous validation techniques and provides better results. With the present method of measuring the pressure of each filter individually or each cluster or section of filters, it is essentially excluded that a defective filter would go unnoticed. The present method therefore supplements the previous validation techniques and makes them more reliable.

The present method is particularly suitable for sterile filtration systems where the filter material of the filter elements is of the membrane type. Such filter membrane material will present a barrier to bacteria or to microorganisms possibly contained in the fluid to be filtered. The present method and filter assembly therefore is particularly suited but not limited to application in the beverage and pharmaceutical industries.

It is also contemplated that the entire method be fully automated. The necessary servo-mechanisms for controlling the valves for gas inlet and outlet belong to the filtration system. Means for the measurement of pressure build-up are well-known in the art. Computational means for performing the comparisons of measured and desired rates and pressures are also well-known in systems control.

What is claimed is:

1. A method of testing the integrity of a filter element in a filter assembly comprising the steps of:
   a) wetting filter material of a filter element having an inlet side and an outlet side connected to an outlet conduit,
   b) subjecting the inlet side of the filter element to a gas pressure,
   c) measuring the pressure in the outlet conduit as a function of time with a downstream outlet valve for the outlet conduit closed wherein the gas pressure at the inlet side of the filter is held at a constant value during said pressure measuring step, and
   d) determining whether the pressure measured at a preselected time exceeds a reference pressure by a predetermined amount.

2. The method of claim 1, wherein the filter element is installed in a filter assembly including a plurality of filter elements connected to the outlet conduit, further comprising measuring the gas diffusion flow rate through the wetted filter material while subjecting all the filter elements in the filter assembly to the gas pressure.

3. The method of claim 2 wherein measuring the gas diffusion flow rate comprises measuring an amount of gas supplied to the filter assembly in order to maintain a constant test gas pressure.

4. The method of claim 1 wherein the filter element is installed in a filter assembly including a plurality of filter elements sub-divided into a plurality of sections, the filter elements of each section are connected to a common outlet conduit, the pressure in step c) is measured in the outlet conduit of each of the sections of filter elements, and the determination in step d) is made for each of the sections of filter elements.

5. The method of claim 4 wherein steps c) and d) are carried out simultaneously for all of the plurality of filter sections.

6. The method of claim 4 wherein the reference pressure for each section is the pressure measured in one of the other of the plurality of filter sections.

7. The method of claim 4 wherein the reference pressure for each section is an average of the pressure measured in at least two of the other filter sections.

8. The method of claim 1 wherein the reference pressure is a preset fixed value.

9. The method of claim 1 wherein the gas pressure is in the range of 50 to 6000 mbar.

10. The method of claim 9 wherein the normal pressure in the outlet conduit is different from atmospheric pressure and the measured gas pressure represents a pressure gradient across the wetted filter material.

11. The method of claim 9 wherein the gas pressure is in the range 500 to 5200 mbar.

12. The method of claim 1 wherein the filter element has been subjected to a sterilization at high temperatures prior to the integrity testing.

13. The method of claim 1 wherein the inlet side of the filter element is subjected to air.

14. A filter assembly for use in testing the integrity of a filter element comprising:
   a plurality of filter elements sub-divided into a plurality of sections, each section containing a portion of the filter elements, each filter element having an outlet side,
   a plurality of outlet conduits each connected to the outlet sides of the filter elements in one of the sections,
   pressure sensing means for measuring the pressure in each outlet conduit,
   a plurality of valves each arranged in the outlet conduit of one of the sections downstream of the pressure sensing means, and
   a common vessel in which the plurality of filter elements are arranged and containing a fluid to be filtered, each filter element having a filter material surface in direct contact with the fluid to be filtered.

15. The filter assembly of claim 14 wherein each section of filter elements comprises 2 to 15 filter elements.

16. The filter assembly of claim 15 wherein each section of filter elements comprises 3 to 7 filter elements.

17. The filter assembly of claim 14 including a controller responsive to the pressure sensing means for determining the integrity of each section by comparing a relationship between time and the pressure measured by the pressure sensing means in a state in which at least one of the valves is closed with a reference relationship between time and pressure.

18. The filter assembly of claim 17 wherein the controller comprises means for comparing the measured pressure at a preselected time with a reference pressure corresponding to the preselected time according to the reference relationship.

19. The filter assembly of claim 17 wherein the controller comprises means for comparing the time required to reach a preselected pressure with a reference time corresponding to the preselected pressure according to the reference relationship.

20. A method of testing the integrity of a filter element in a filter assembly, the filter assembly comprising a plurality of filter elements divided into a plurality of sections and a plurality of outlet conduits each connected to one of the sections, the method comprising the steps of:
   a) wetting filter material of each filter element,
   b) applying a gas pressure to the inlet side of each filter element,
   c) measuring the pressure in each outlet conduit as a function of time with a downstream outlet valve for each outlet conduit closed wherein the gas pressure at the inlet side of each filter element is held at a constant value during said pressure measuring step, and
   d) determining the integrity of each section by comparing a relationship between the measured pressure and time for each section with a reference relationship including comparing the time required to reach a preselected pressure with a reference time corresponding to the preselected pressure according to the reference relationship.

21. A method of testing the integrity of a filter element in a filter assembly comprising the steps of:
   a) wetting filter material of a filter element having an inlet side and an outlet side connected to an outlet conduit,
   b) subjecting the inlet side of the filter element to a gas pressure,
   c) measuring the pressure in the outlet conduit as function of time with a downstream outlet valve for the outlet conduit closed, wherein the gas pressure is held at a constant value during said pressure measuring step, and
   d) determining whether the time required to reach preselected pressure is shorter than a reference time by a predetermined amount.

22. The method of claim 21, wherein the filter element is installed in a filter assembly including a plurality of filter elements connected to the common outlet conduit, further comprising measuring the gas diffusion flow rate through the wetted filter material while subjecting all the filter elements in the filter assembly to the gas pressure.

23. The method of claim 22 wherein measuring the gas diffusion flow rate comprises measuring an amount of gas supplied to the filter assembly in order to maintain a constant test gas pressure.

24. The method of claim 21 wherein the filter element is installed in a filter assembly including a plurality of filter elements subdivided into a plurality of sections, the filter elements of each section are connected to a common outlet conduit, the pressure in step c) is measured in the outlet conduit of each of the sections of filter elements, and the determination in step d) is made for each of the sections of filter elements.

25. The method of claim 24 wherein steps c) and d) are carried out simultaneously for all of the plurality of filter sections.

26. The method of claim 21 wherein the gas pressure is in the range of 50 to 6000 mbar.

27. The method of claim 21 wherein the normal pressure in the outlet conduit is different from atmospheric pressure and the measured gas pressure represents a pressure gradient across the wetted filter material.

28. The method of claim 21 wherein the filter element has been subjected to a sterilization at high temperatures prior to the integrity testing.

29. The method of claim 21 wherein the gas pressure is in the range 500 to 5200 mbar.

30. The method of claim 21 wherein the inlet side of the filter element is subjected to air.

* * * * *